US006895279B2

(12) United States Patent
Loeb et al.

(10) Patent No.: US 6,895,279 B2
(45) Date of Patent: May 17, 2005

(54) METHOD AND APPARATUS TO TREAT DISORDERS OF GASTROINTESTINAL PERISTALSIS

(75) Inventors: Gerald E. Loeb, South Pasadena, CA (US); Frances J. R. Richmond, South Pasadena, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 261 days.

(21) Appl. No.: 09/953,425

(22) Filed: Sep. 14, 2001

(65) Prior Publication Data

US 2002/0123774 A1 Sep. 5, 2002

Related U.S. Application Data

(60) Provisional application No. 60/232,753, filed on Sep. 15, 2000.

(51) Int. Cl.[7] .............................................. A61N 1/08
(52) U.S. Cl. ...................................................... 607/40
(58) Field of Search ............................... 600/373, 377; 607/40, 59, 60, 65, 133; 128/903

(56) References Cited

U.S. PATENT DOCUMENTS

| | | | |
|---|---|---|---|
| 4,134,408 A | | 1/1979 | Brownlee et al. |
| 5,193,539 A | | 3/1993 | Schulman et al. |
| 5,193,540 A | * | 3/1993 | Schulman et al. ............ 607/61 |
| 5,312,439 A | | 5/1994 | Loeb et al. |
| 5,324,316 A | | 6/1994 | Schulman et al. |
| 5,405,367 A | | 4/1995 | Schulman et al. |
| 5,423,872 A | | 6/1995 | Cigaina |
| 5,697,076 A | | 12/1997 | Troyk et al. |
| 5,836,994 A | | 11/1998 | Bourgeois |
| 5,861,014 A | | 1/1999 | Familoni |
| 5,995,872 A | | 11/1999 | Bourgeois |
| 6,026,326 A | * | 2/2000 | Bardy .......................... 607/40 |
| 6,051,017 A | | 4/2000 | Loeb et al. |
| 6,061,596 A | | 5/2000 | Richmond et al. |
| 6,104,955 A | | 8/2000 | Bourgeois |
| 6,185,452 B1 | * | 2/2001 | Schulman et al. ............ 604/20 |
| 6,238,423 B1 | | 5/2001 | Bardy |
| 6,240,316 B1 | * | 5/2001 | Richmond et al. ............ 607/42 |
| 6,327,503 B1 | | 12/2001 | Familoni |
| 6,345,202 B2 | | 2/2002 | Richmond et al. |
| 6,582,441 B1 | * | 6/2003 | He et al. ..................... 606/129 |
| 2002/0072779 A1 | * | 6/2002 | Loeb .......................... 607/40 |

OTHER PUBLICATIONS

R.W. McCallum et al. Gastric pacing improves emptying and symptoms in patients with gastroparesis. Gastroenterology 1998; vol. 114: pp. 456–461.

Aizawa, M. Optical fiber electrodes for electrochemical luminescence–based homogeneous immunoassay. In Biosensor Technology Fundamentals and Applications. R.P. Buck et al., editors. New York: Marcel Dekker, Inc., pp. 209–218.

(Continued)

Primary Examiner—Jeffrey R. Jastrzab
Assistant Examiner—Frances P. Oropeza
(74) Attorney, Agent, or Firm—McDermott Will & Emery LLP

(57) ABSTRACT

Many patients suffer from diseases and surgical damage that result in failure of the stomach and intestinal tract to contract and relax normally in order to transfer contents distally. Electrical stimulation applied to one or more sites on the surface of the gastrointestinal viscera can treat this problem by triggering or altering muscle contractility. The present invention provides such stimulation by implanting leadless microstimulators in or on the walls of the viscera that can be programmed or controlled from a source outside the body.

12 Claims, 1 Drawing Sheet

OTHER PUBLICATIONS

Abdel–Latif, M.S. Fiber optic–based biosensors utilizing immobilized enzyme systems. In Biosensor Technology Fundamentals and Applications. R.P. Buck et al., editors. New York: Marcel Dekker, Inc., pp. 285–298.

Bellahsene, B.–E. et al. Acceleration of gastric emptying with electrical stimulation in a canine model of gastroparesis. 1992. American Journal of Physiology 226: G826–G834.

Fontana, R.J. et al. Jejunostomy tube placement in refractory diabetic gastroparesis: A retrospective review. 1996. The American Journal of Gastroenterology 91: 2174–2178.

Garry, R.C. et al. Reflexes involving the external urethral sphincter in the cat. J. Physiol. 1959. vol. 149: pp. 653–665.

Gems Study Group. Electrical stimulation for the treatment of gastroparesis—preliminary repor of a multicenter international trial. (Abstract.) 1996. Gastroenterology 10(4): A668.

Gems Study Group. Long–term results of gastric stimulation four times higher than the slow wave frequency in patients with drug–refractory gastroparesis. (Abstract.) 1999. Gastroenterology 116: G4131.

Goswami, K. et al. Fiber optic chemical sensors (FOCS): An answer to the need for small, specific monitors. In Biosensor Technology Fundamentals and Applications. R.P. Buck et al., editors. New York: Marcel Dekker, Inc., pp. 299–310.

Hasler, W.L. Editorial: The brute force approach to electrical stimulation of gastric emptying: A future treatment of refractory gastroparesis? 2000 Gastroenterology 118: 433–436.

Janssens, J. et al. Improvement of gastric emptying in diabetic gastroparesis by erythromycin. 1990. The New England Journal of Medicine 322: 1028–1031.

Luo, J. et al. Gastric electrical stimulation improves both GI symptoms and gastric emptying in patients with "post–surgical" gastroparesis. (Abstract.) 1999. Gastroenterology 116: S0162.

Mintchev, M. et al. Computer model of gastric electrical stimulation. 1997. Annals of biomedical engineering 25: 726–730.

Snape, W.J., Jr. et al. Metoclopramide to treat gastroparesis due to diabetes mellitus: A double–blind, controlled trial. 1982. Annals of internal medicine 96: 444–446.

Sturm, A. et al. Treatment of patients with gastroparesis: A meta–analysis of prokinetics. (Abstract.) 1997. Gastroenterology 112: A833.

Tabbaa, M. et al. Gastric electrical stimulation rapidly improves nutritional depletion in gastroparesis. (Abstract.) 1999. Gastroenterology 116: G2543.

Tack, J. et al. The influence of gastric electrical stimulation on proximal gastric motor and sensory function in severe idiopathic gastroparesis. 1999. Gastroenterology 116: G4733.

* cited by examiner

METHOD AND APPARATUS TO TREAT DISORDERS OF GASTROINTESTINAL PERISTALSIS

RELATED APPLICATIONS

This application claims the filing date benefit of U.S. Provisional Application No. 60/232,753, filed on Sep. 15, 2000, entitled "Method and Apparatus to Treat Disorders of Gastrointestinal Peristalsis," and relates to U.S. Provisional Application No. 60/230,664, filed on Sep. 7, 2000, entitled "Method and Apparatus for Control of Bowel Function," and U.S. patent application Ser. No. 09/949,424, filed on Sep. 7, 2001, now U.S. Pat. No. 6,658,297, issued Dec. 2, 2003, entitled "Method and Apparatus for Control of Bowel Function," the contents of which are incorporated herein.

BACKGROUND OF THE INVENTION

1. Field of the Invention

This invention relates to gastrointestinal disorders. More particularly, this invention relates to treatment of gastrointestinal disorders by using a method and apparatus for providing electrical stimulation of the gastrointestinal tract.

2. General Background and State of the Art

The reception of nutrition in the human body is an essential step of the digestive process which is performed by the gastrointestinal tract. An important element in the digestive process is gastric and intestinal peristalsis, the coordinated and locally controlled contractions that propel food and wastes through the various stages of digestion and excretion. Peristalsis is accomplished through a coordinated combination of mechanical, electrical, chemical, and hormonal mediation.

Gastroparesis is a chronic disorder of the stomach, defined as delayed gastric emptying of a solid meal. Symptoms of gastroparesis range from early satiety and nausea in mild causes to chronic vomiting, dehydration, and nutritional compromise in severe cases. A series of experimental studies in various animal models has described various loci and patterns of electrical stimulation that might be capable of producing the desired gastrointestinal contractions in patients with conditions such as gastroplegia (stomach paralysis) or gastroparesis (stomach weakness). The more common forms of human gastroparesis, for example, appear to be associated with loss of the vagal innervation of the stomach, which should leave intact the intrinsic sympathetic circuitry within the stomach walls that coordinates peristalsis.

Thus, one or a small number of stimulation channels should be effective in stimulating activity initiated in the gastric pacemaker. However, the previously available technology for electrical stimulation makes it difficult even to conduct research in human subjects, much less to provide them with a long term treatment. Most of the studies have employed short-term percutaneous leads. The scientific literature includes descriptions of clinical experiments, but the experimental designs have been compromised by the limitations of the available technology and the results are inconclusive.

Previously available implantable clinical stimulators as described, for example, in U.S. Pat. Nos. 5,861,014 and 5,995,872, require electrical leads to conduct stimulation pulses from a relatively large electrical pulse generator to electrodes affixed to the desired stimulation site. However, the large amount of motion between the stomach and adjacent structures makes it impractical to maintain such leads.

At the other end of the gastrointestinal tract, similar disorders of peristalsis result in constipation or retention of feces in the colon and rectum. Conversely, excessive motility of the colon leads to diarrhea and clinical disorders such as colitis and "dumping syndrome" in which patients are unable to retain food in their gastrointestinal tracts long enough for proper digestion and absorption. Neuroscientists believe that various parasympathetic and sympathetic neural circuits exist to initiate or inhibit the natural peristalsis rhythm generators within the walls of the colorectal system. Electrical stimulation applied in the vicinity of these neurons could be used to activate such circuits and restore the desired level of motility, much as a cardiac pacemaker maintains regular beating of the heart.

SUMMARY OF THE INVENTION

The present invention therefore provides for an improved method of treating clinical gastrointestinal emptying disorders using electrical stimulation. The present invention employs methods and devices for electrical stimulation that do not require electrical leads to connect electronic circuitry in one location to stimulation electrodes located at a different site. The present achieves this by using the function, form and detailed design of such microstimulators which are described in detail by U.S. Pat. No. 6,051,017 which is incorporated herein by reference. The present invention therefore provides an apparatus and method that is wireless, to power and control the electrical stimulation of the stomach from outside the body.

A new class of implantable medical device, known as the BION™ microstimulator, makes it possible to create accurately localized and precisely graded electrical fields within virtually any body structure. Each BION includes electrical stimulation circuitry and electrodes configured in a form factor that is suitable for injection through a hypodermic needle. There are no attached leads to receive power or commands or to route stimulation pulses to distant electrodes. BIONs receive power by inductive coupling to an externally applied RF magnetic field. They receive digital command signals by detecting and decoding modulations of the RF carrier. The electronic circuitry in the BION may use the power and data immediately to generate the required electrical stimulation currents in the adjacent tissue by passing current through the integral electrodes, or it may store power and data by various conventional means to enable the generation of output pulses when the RF field is not present. The packaging and materials of the BION are selected and designed to protect its electronic circuitry from the body fluids and to avoid damage to the electrodes and the surrounding tissues from the presence and operation of the BION in those tissues. Thus, BION implants are well suited to delivering well-controlled and stable electrical stimulation to nerves in sites that are not amenable to stimulation by conventional technologies as described above.

The present invention makes use of leadless microstimulators, such as the BION microstimulator to provide electrical stimulation to areas of the gastrointestinal tract in the hopes of treating various neuromuscular disorders. In an exemplary embodiment of the present invention, a leadless microstimulator is implanted in a patient's body. In the present invention, the leadless microstimulator is implanted in or on the muscular walls of the gastrointestinal tract so as to effect a desired stimulation of the gastrointestinal tract. In the case of gastroparesis or gastroplegia, one likely implantation site would be the serosal wall of the stomach in the region of the fundus. In the case of fecal retention, one likely implantation site would be the serosal wall of the descending colon and/or rectum. The patient is also provided with a controller located external from the body which is operated when the desired stimulation is wanted. The controller provides power and command signals to the leadless microstimulator. The microstimulator receives these power and command signals from the controller and translates the signals into electrical pulses which are generated. The implants may use these power and command transmissions immediately to generate stimulation pulses or the implants may incorporate rechargeable batteries and data memory circuitry enabling them to generate preprogrammed stimulation sequences for a period of hours to days even when no external control or power source is present.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE EXEMPLARY EMBODIMENTS

Figure 1:
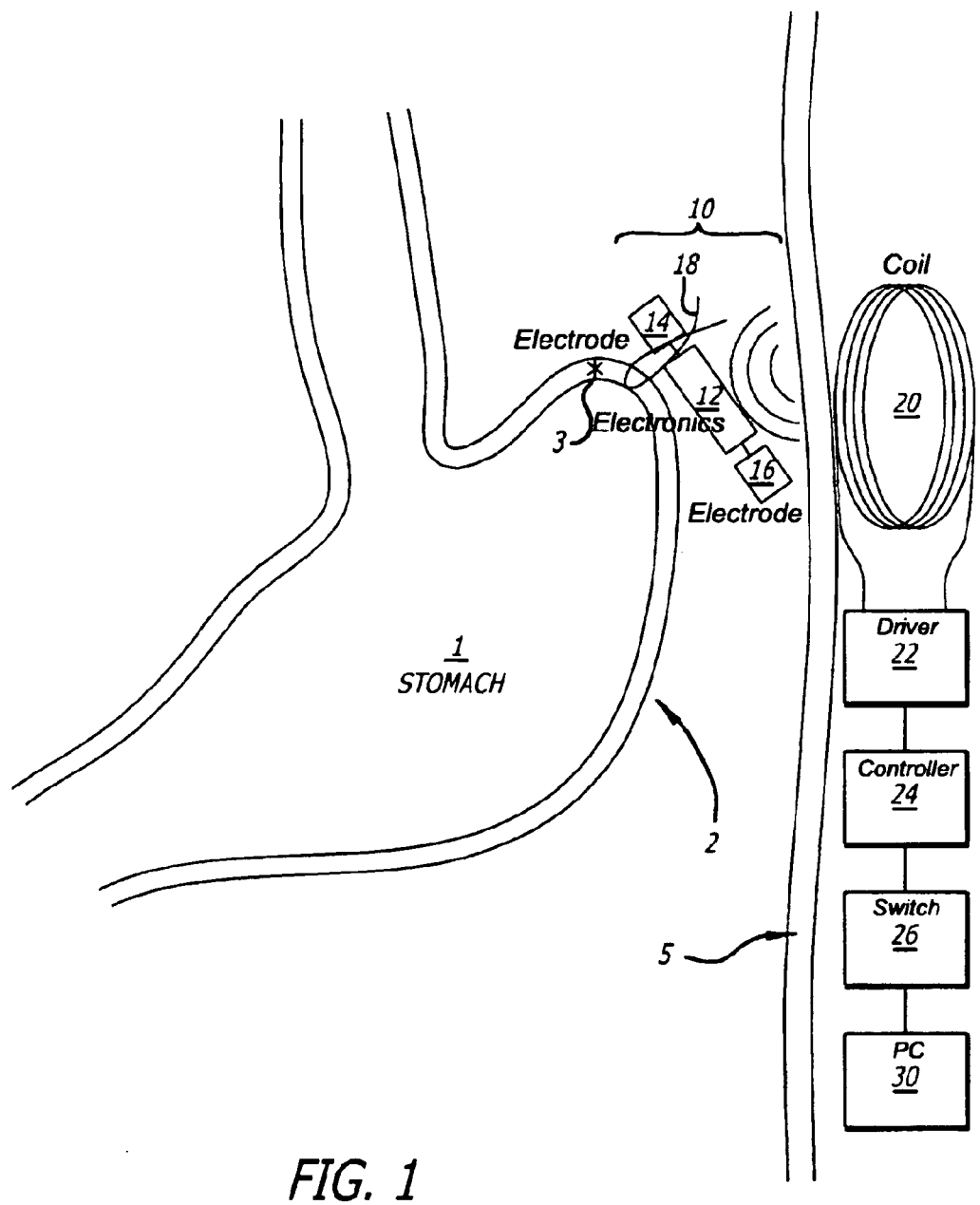
FIG. 1 is a schematic of an embodiment of the present invention which displays an exemplary position for implantation of a microstimulator for use in the present invention.

The following description is of the best mode presently contemplated for carrying out the invention. This description is not to be taken in the limiting sense, but is made merely for the purpose of describing the general principles of the invention. The scope of the invention should be determined solely by the claims.

In an exemplary embodiment of the present invention, one or more microstimulators (10) are implanted in or on the wall (2) of stomach (1) as illustrated in FIG. 1. Said microstimulators (10) are advantageously of a size and shape to be implantable through the lumen of a flexible tube, a rigid hypodermic needle, a laparoscope, endoscope or any other suitable type of medical delivery device. In a preferred embodiment, said microstimulators (10) are approximately 2 mm diameter by 16 mm length, or approximately 0.5 mm to 1 mm or greater in diameter, and by about 2 to 18 mm, or about 14 to 16 mm, or greater, in length. The function, form and detailed design of such microstimulators have been described in detail previously by U.S. Pat. No. 6,051,017 which is incorporated herein by reference. Microstimulators that contain a rechargeable battery capable of powering them for hours to days in the absence of an external electromagnetic field would probably be somewhat larger. The present state of the art of battery technology suggests that such an implant would have to be approximately 3 mm in diameter and 22 mm long to accommodate such rechargeable battery technology. A larger, battery-powered implant would still be implantable by means similar to those described in this exemplary embodiment and falls within the scope of the invention taught herein.

One implantation route for said microstimulators (10) would be intramural injection from the mucosal surface as accessed by a nasogastric or gastroscopy tube or endoscope. Another implantation route would be intramural injection from the serosal surface via a laparoscopy tool or by open surgery. Yet another implantation route would be attachment to the serosal wall of the gastrointestinal tract with a fixation device (18) such as a surgical clip, suture, or staple, either during open laparotomy or via laparoscopic instruments. The number and location of microstimulators (10) deployed would depend on the nature of the underlying pathophysiology of the motility disorder. Where conditions permit, it would be advantageous to locate a microstimulator (10) at or near the site of a physiological pacemaker (3) such that electrical activation of said pacemaker site (3), here depicted in FIG. 1 near the fundus of the stomach, would lead to orderly spread of a wave of propulsive peristalsis throughout the stomach.

Each microstimulator (10) consists of three major elements: electronic subassembly (12) and two electrodes (14 and 16). Electronic subassembly (12) receives power and command signals by inductive coupling from transmission coil (20) located outside the body wall (5). When the patient desires the stomach to empty, for example after eating a meal, the patient places transmission coil (20) sufficiently close to all microstimulators (10) so as to be able to transmit sufficient power to operate them. The patient then manually operates a switch (26) to initiate the operation of transmission coil (20) with a carrier frequency generated by driver (22) and modulated according to a pattern that has been loaded into digital memory means contained within controller (24). The modulation pattern conveys data representing a string of command signals that cause each microstimulator (10) to generate stimulation pulses with the appropriate timing and intensity to evoke the desired stomach contraction. Alternatively, the microstimulator can be operated by an automated system. Such a system would comprise a sensor for sensing the need for emptying of the stomach or rectum, such as detecting presence of solid matter or physical distension, and would be capable of effecting microstimulator activity in response.

During the initial implantation, it may be advantageous to test the efficacy of potential sites for the implantation of microstimulators (10) by applying stimulation pulses through conventional electrodes that can be incorporated into or passed temporarily through the instruments used for implantation. The modular design and addressability of said microstimulators (10) is advantageous because it permits additional channels of stimulation to be added to the patient at any time without interfering with those channels installed previously. After implantation, the design of an effective pattern of stimulation pulses can be accomplished by variously activating the implanted microstimulators (10) via the transmission coil (20) while observing the motion of the stomach with conventional imaging techniques such as x-ray fluoroscopy, CT scan or real-time ultrasound. This is best performed by a more sophisticated user interface such as could be provided by application-specific software running on, for example, a personal computer (30) that is connected temporarily to controller (24).

The present invention also includes use of microstimulators for treating motility dysfunctions at sites other than the stomach. For example, motility dysfunction in other parts of the entire gastrointestinal tract, such as in the esophagus, small intestine (e.g. ileum, duodenum), or large or small bowel, or rectum, may be treated by implanting the present invention at those sites. In particular, many patients suffer from inability to move partially digested food and feces along parts of the esophagus, ileum, the colon and the rectum, resulting in a variety of secondary medical problems including reflux, malabsorption, constipation and impaction. By implanting one or more microstimulators (10) in or on these structures, it should be possible to activate local pacemaking circuits of neurons that will result in the desired peristaltic wave. These and other related gastrointestinal dysfunctions and sites of stimulation are within the scope of our invention.

The present invention also includes use of microstimulators for treating motility dysfunctions such as those resulting from injury to the patient's nervous system. For example, microstimulators of the present invention will be used to treat fecal retention and constipation that result frequently from neurological injuries to the spine and from surgical damage to the intestinal innervation during surgical procedures such as in resections of a patient's tumor.

It is also contemplated that the present invention includes use of microstimulators for treating motility dysfunctions due to hypermotility of the gastrointestinal tract. In such a use, the microstimulators would effectively dampen or "repace" the gastrointestinal tissue so as to result in a normalized spread of peristalsis. The use of electrical stimulation to reduce hypermotility by resetting pacemaker or peristaltic activity in such a setting would be similar to that employed, for example, using implanted pacemakers and defibrillators to prevent heart muscle arrhythmias.

It should be noted that the present invention is not limited only to those microstimulators described in the above referenced patent, or the BION microstimulator as described above, but should include other types of lead less implantable microstimulators as well. It is contemplated to be within the scope of the present invention to use microstimulator devices having varying configurations. For example, microstimulators having improved power storage means such as a tiny rechargeable battery, are currently being developed. These microstimulators are able to autonomously generate stimulation pulses even when an RF coil is not present.

The main feature is the use of a wireless miniature device that can be affixed directly to the moving gut without requiring leads for electrodes, power or command signals. Other features include the elongated form factor, which permits implantation through a tube, sheath, trocar, catheter or needle, and the ability to combine and selectively control multiple implants to produce a phase-sequence of activation that may be necessary to achieve proper peristalsis in some forms of pathophysiology.

As would be apparent to one skilled in the art, variations in the design and function of the implantation and fixation tools as well as the equipment and procedures used for fitting a stimulation program for use with the present invention can be made depending on user preference, patient need or treatment modality desired. Particular patterns of stimulation can be applied using a particular microstimulator or combination of microstimulators adapted for use with an external control system.

We claim:

1. An apparatus for providing stimulation to the gastrointestinal tract comprising: a leadless microstimulator adapted to be implanted in or on a wall of a patient's stomach; and a controller located outside the body of the patient for transmitting a signal and power to the microstimulator, comprising: a transmission coil wirelessly coupled to the microstimulator; memory means for storing modulated signal patterns; a driver coupled to the transmission coil for generating a carrier frequency according to the modulated signal patterns located in the memory means; and a switch operable by the patient for initiating operation of the transmission coil, causing each microstimulator to generate pulses with an appropriate timing and intensity to evoke a desired contraction.

2. The apparatus of claim 1 wherein the leadless microstimulator is a class of microstimulator operable by a continuous RF field.

3. The apparatus of claim 1 wherein the leadless microstimulator is adapted to be implanted into the stomach for treatment of gastroparesis.

4. The apparatus of claim 1 wherein the leadless microstimulator is adapted to be implanted contacting tissue in at least one of the group consisting of: stomach, esophagus, small intestine, large bowel, small bowel, and rectum.

5. A method for treating disorders of gastrointestinal peristalsis, comprising: implanting a leadless microstimulator in or on the wall of a patient's stomach, wherein said leadless microstimulator is adapted to be implanted in or on the wall of a patient's stomach; providing the patient with a controller providing power and command signals to the microstimulator upon operation; and electrically stimulating the area of the gastrointestinal tract where the leadless microstimulator is adapted to be implanted so as to excite a physiological response from tissue near the microstimulator.

6. The method of claim 5 wherein the leadless microstimulator is implanted through injection from the serosal surface via a laparoscopy tool.

7. The method of claim 5 wherein the leadless microstimulator is implanted through an endoscope.

8. The method of claim 5 wherein the leadless microstimulator is adapted to be attached to the serosal wall of the gastrointestinal tract with a surgical clip.

9. The method of claim 5 wherein the leadless microstimulator is adapted to be attached to the serosal wall of the gastrointestinal tract with a suture.

10. The method of claim 5 wherein the leadless microstimulator is adapted to be attached to the serosal wall of the gastrointestinal tract with a staple.

11. The method of claim 5 wherein the leadless microstimulator is implanted near the fundus of the stomach.

12. An apparatus for treating disorders of stomach peristalsis, the apparatus comprising: a leadless microstimulator adapted to be implanted in or on the wall of the stomach near the fundus; and a controller located outside the body of the patient for transmitting a signal and power to the microstimulator, comprising: a transmission coil wirelessly coupled to the microstimulator; memory means for storing modulated signal patterns; a driver coupled to the transmission coil for generating a carrier frequency according to the modulated signal patterns located in the memory means; and a switch operable by the patient for initiating an operation of the transmission coil, causing the microstimulator to generate pulses with an appropriate timing and intensity to evoke a peristaltic contraction in the stomach.

* * * * *